United States Patent [19]

Chen

[11] Patent Number: 5,195,517
[45] Date of Patent: Mar. 23, 1993

[54] ACUPUNCTURE POINT DISPLAY TYPE ELECTRIC STIMULATING THERAPEUTIC DEVICE

[76] Inventor: I-Cheng Chen, 2F1. No. 6 Alley 8, Szewei Lane, Chung Cheng Road, Hsin-Tien City, Taipei Hsien, Taiwan

[21] Appl. No.: 761,238

[22] Filed: Sep. 17, 1991

[51] Int. Cl.⁵ .................... A61N 1/00; A61H 39/02
[52] U.S. Cl. ........................... 128/419 R; 128/907; 128/735
[58] Field of Search ................ 128/421–422, 128/419 R, 907, 735

[56] References Cited

U.S. PATENT DOCUMENTS 4,895,149  1/1990  Morez .................. 128/419 R
4,966,164  10/1990 Colsen et al. .............. 128/789
4,989,605  2/1991  Rossen .................... 128/422

FOREIGN PATENT DOCUMENTS 2512234  4/1976  Fed. Rep. of Germany ...... 128/907

*Primary Examiner*—Lee S. Cohen
*Assistant Examiner*—Jeffrey R. Jastrzab
*Attorney, Agent, or Firm*—Bacon & Thomas

[57] ABSTRACT

An acupuncture point display type electric stimulating therapeutic device is disclosed having a casing, an acupuncture point display system, an electric stimulating and heat generation system, and a power supply. The casing is divided into two parts: an upper casing and a lower casing. The upper casing has a hollow interior space, and has a recessed display, while the lower casing has control switches, adjusting knobs and connectors on its top surface. The upper and lower casings are connected together by a connecting element and locked together in the form of a book by a tenon and a mortise connection. The acupuncture point display system is installed within the upper casing, the electric stimulating and heat generation system is located within the lower casing, and the power supply provides electric power to all the systems. By entering a code representing the disorder to be treated, a description of the disorder, names and locations of the acupuncture points and a figure showing the locations of such acupuncture points on a human body are displayed as a reference for application of the electric therapeutic devices and/or heat curing plates for therapy purposes.

14 Claims, 3 Drawing Sheets

ACUPUNCTURE POINT DISPLAY TYPE ELECTRIC STIMULATING THERAPEUTIC DEVICE

BACKGROUND OF THE INVENTION

The present invention relates to an acupuncture point display type electric stimulating therapeutic device, particularly an electric stimulating device and heat curing device to be applied to acupuncture points on human body with reference to a display of locations of such acupuncture points on human body as set up by a microprocessor.

A sense of uncomfortableness or disorder is unavoidable in our living, especially in a complex society today. The progress of medical science has allowed the human being to survive ever longer, and relieve a lot of human beings from pain. However, treatment with medicine can bring side-effects, and extensive use of medicine may cause abnormal function of organs. Acupuncture is a therapy developed in China which can prevent disorder and cure disease without side-effects or with only negligible side-effects. However, as its theories are very sophisticated, a person who has never received professional training in this field can't locate the exact position of each acupuncture point and they are not aware of the acupuncture points to be applied for each particular disorder. Therefore, treatment with acupuncture is difficult.

In 1825, Sarlandiere, used a low frequency electric stimulating needle to treat rheumatism and neurological disorders. It was the first use of an electric device with the principle of acupuncture. In the view point of the principles of main meridians and muscle meridians in Chinese medicine, and the nervous reflection upon application pressure, a low frequency can provide a stimulating effect to the human body, and it can change the resistance at an acupuncture point because the resistance there is smaller than the resistance around the acupuncture point. Hence, the application of a low frequency can provide a balance and restriction effect.

SUMMARY OF THE INVENTION

In view of the need in locating the exact position of each acupuncture point, the inventor created an acupuncture point display type electric stimulating therapeutic device which can display the position of each acupuncture point on the human body with the help of a microprocessor so that the name and location of each acupuncture point corresponding to each particular disorder is displayed and then a suitable low frequency electric therapeutic device and/or heat curing plate can be correctly applied by referring to the display. In other words, the present invention can display the name and location of an acupuncture point to be treated for each particular disorder so that the operator can locate the exact position of such acupuncture point easily for electric stimulating or heat curing, and the patient can be treated without any sense of pain.

BRIEF DESCRIPTION OF THE DRAWINGS

These and other objects and features of the invention will become more apparent from the following description taken in connection with the accompanying drawings wherein.

DETAILED DESCRIPTION OF THE PREFERRED EMBODIMENTS

Figure 1:
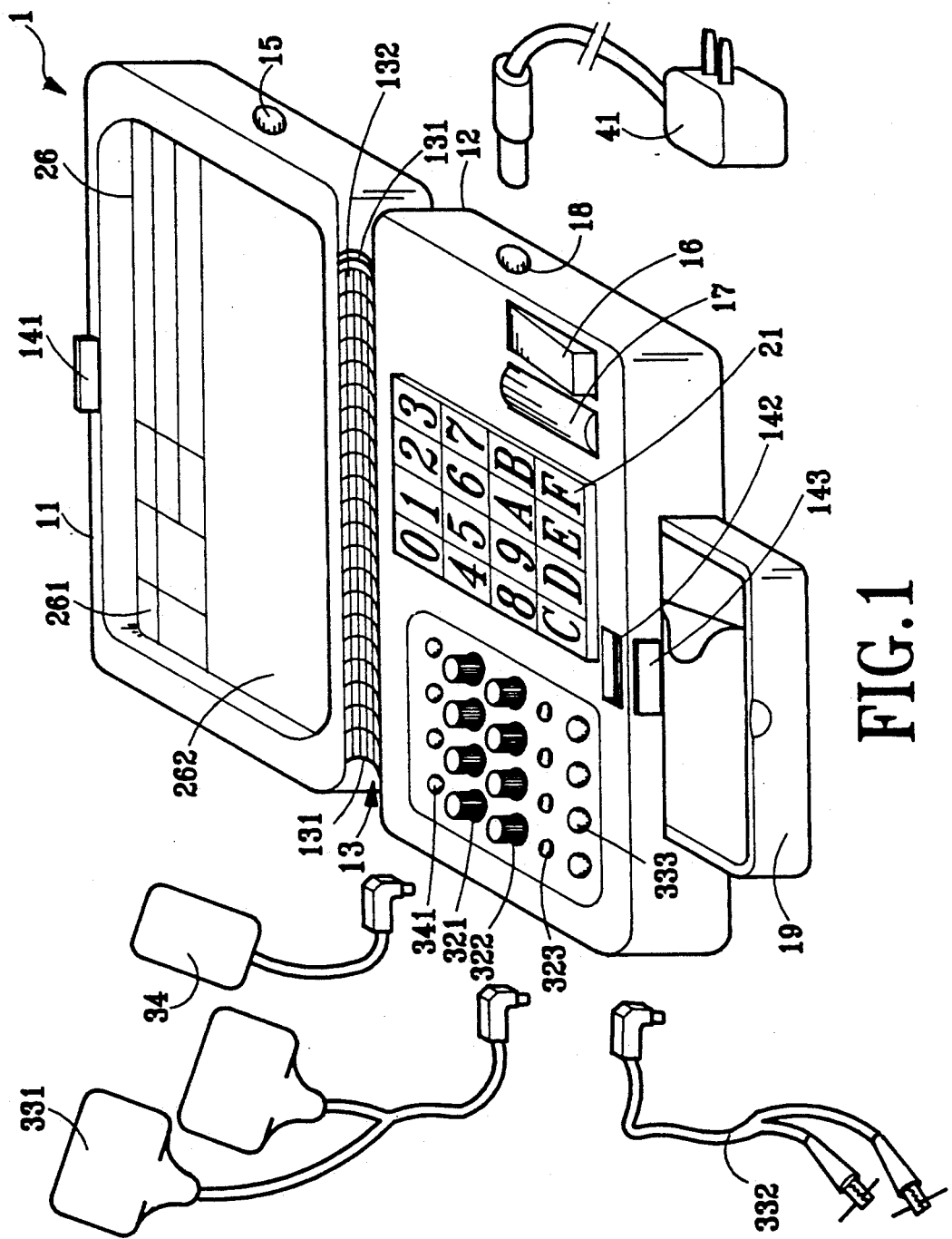
FIG. 1 is a perspective view of an acupuncture point display type electric stimulating therapeutic device according to the present invention.

Please refer to FIG. 1, a perspective view of an acupuncture point display type electric stimulating therapeutic device according to the present invention, the casing (1) is divided into two parts: an upper casing (11) and a lower casing (12). The upper casing (11) has a hollow interior space for installation of an acupuncture point display system (2). On its surface there is a recessed display (26) and a tenon (141). A socket (15) for connecting to a computer is designed on a side of the upper casing (12) for display of locations of acupuncture points. The lower casing (12) has a hollow interior space for installation of an electric stimulating and heat generation system (3). On the surface of the lower casing (12) a power source switch (16), a reset switch (17), an input device (21), a plurality of heat curing plate connectors (341), a plurality of voltage regulating knobs (321), a plurality of frequency adjusting knobs (322), a plurality of indicator lamps (323), a plurality of electric therapeutic device connectors (333) and a mortise (142) are arranged. A power input socket (18) is designed at its right side, a box (19) and a release button (143) are designed at the bottom of the lower casing (12). The upper casing (11) and lower casing (12) are connected together by a connecting element (13) and locked together by means of a tenon (141) and a mortise (142) in the form like a book. The connecting element (13) is composed of two retaining rings (131) and a bus wire (132). The box (19) is for holding of stimulating electrodes (331), electric acupuncture needles (332) and heat curing plates (34). The release button (143) is designed to control engagement of the mortise (142) and the corresponding tenon (141). The stimulating electrode (331) and/or the electric acupuncture needles (332) as required can be connected to the electric therapeutic device connectors (333) for electric therapy. The heat curing plate (34) can be connected to the heat curing plate connector (341) for thermal therapy. An AC to DC transformer (41) is used to transform alternating current to direct current as power source connecting to the power input socket (18). After the power source switch (16) is turned on, the electric stimulating and heat generation system (3) works and generates electric curing and heat curing signals required. The strength of the electric curing signal can be adjusted by turning of the voltage regulating knob (321) and the frequency adjusting knob (322) s that a proper strength is obtained. On the other hand, a code representing the disorder to be treated is set up through the input device (21). Then, via the bus wire (132), the acupuncture point display system (2) operates to display on the display (26) a description of the disorder to be treated, names and locations of the related acupuncture points, and a figure representing the locations of such acupuncture points on the human body. Then, by referring to the display, its operator can apply the stimulating electrodes (331), or electric acupuncture needles (332), and the heat curing plates (34) on the corresponding acupuncture points for therapy purposes. Each pushing of the reset switch (17) can reset a microprocessor in the acupuncture point display system (2) to a predetermined condition. The respective indicator lamp (323) shows operations of the corresponding electric therapeutic device (33).

Figure 2:
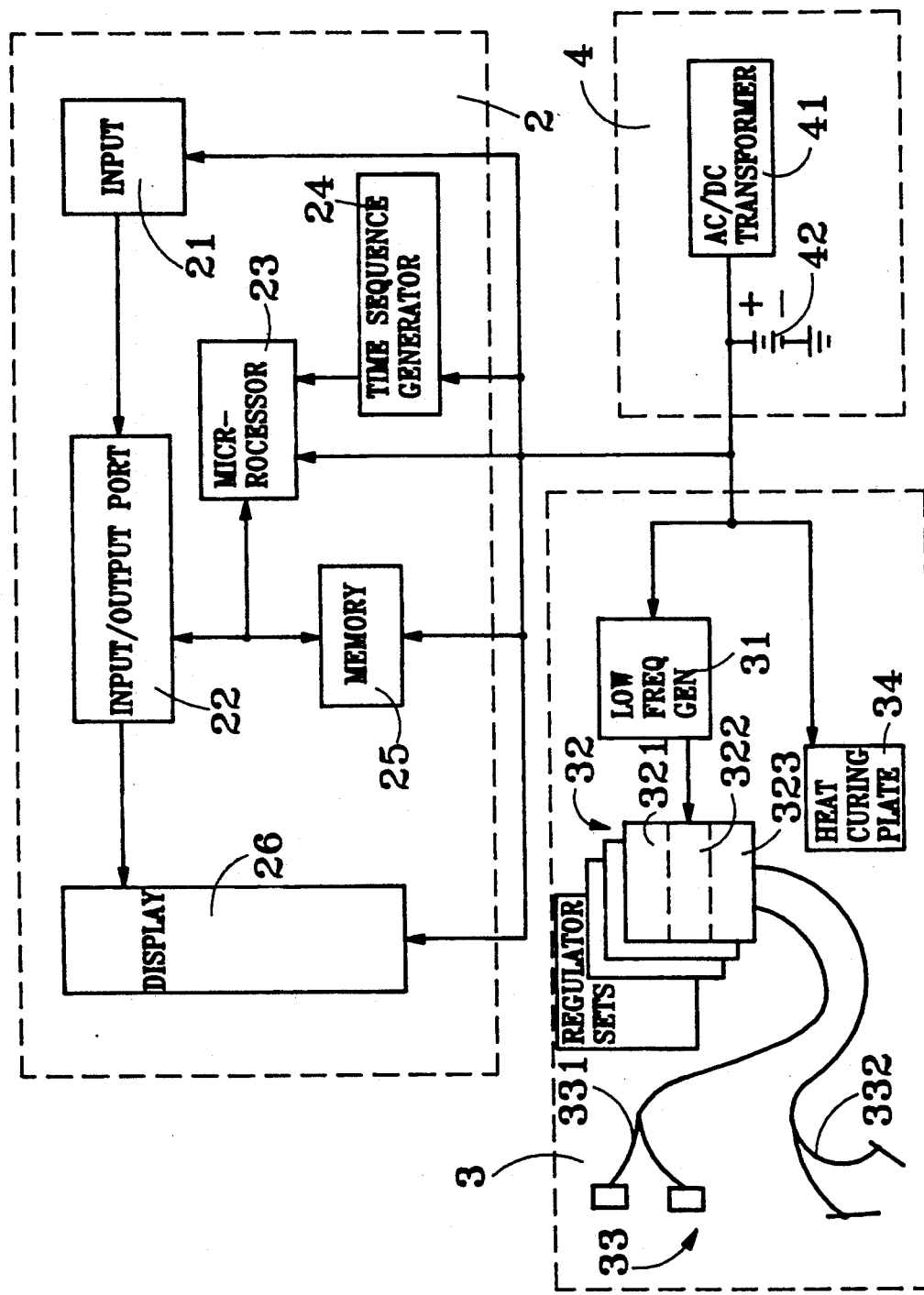
FIG. 2 is a block diagram for the control system of the acupuncture point display type electric stimulating therapeutic device according to the present invention.

Please refer to FIG. 2, a block diagram of the control system for the acupuncture point display type electric stimulating therapeutic device according to the present invention, the control system is composed of the acupuncture point display system (2), the electric stimulating and heat generation system (3) and a power supply (4), functions of which are described hereafter.

1. The acupuncture point display system (2) comprises an input device (21), an input/output port (22), a microprocessor (23), a time sequence generator (24), a memory (25), and a display (26). Upon a control by the microprocessor (23), the locations and descriptions of the respective acupuncture points on the human body are displayed on the display (26). The input device (21) is in the form of a keyboard or a card reader to provide input signal to the microprocessor (23) via the input/output port (22) in 16-bit parallel data. The microprocessor (23) is a chip to serve as the heart of the control system. Upon receipt of a signal from the input/output port (22), it retrieves data from the memory (25), preferably an electric programmable read only memory (EPROM) in which data about display of acupuncture points are stored. The data retrieved from the memory (25) are then sent to the display (26) via the input/output port (22). The display (26) is a LCD, or LED, or other appropriate form of display to display description and positions of the respective acupuncture points, as well as a figure of human body showing the location of each acupuncture point according to signal provided by the input device (21). The time sequence generator (24) is to generate a sequence pulse for operation of the microprocessor (23).

2. The electric stimulating and heat generation system (3) comprises a low frequency generator (31), a plurality of regulator sets (32), a plurality of electric therapeutic devices (33) and a plurality of heat curing plates (34). The low frequency generator (31) can generate a low frequency and high voltage signal, which, after entering the corresponding acupuncture point on human body, can change direct current resistance on the acupuncture point for balancing and restriction purposes. A number of regulator sets (32) are used in the present invention. Each regulator set (32) includes a voltage regulating knob (321), a frequency regulating knob (322) and an indicator lamp (323). The voltage and frequency of each therapeutic signal output can be adjusted according to responses from the human body being treated and to meet different requirements for therapy purposes by turning of the voltage regulating knob (321) and the frequency regulating knob (322). The electric therapeutic devices (33) can be stimulating electrodes (331) and/or electric acupuncture needles (332) connecting to the electric therapeutic device connectors (333) to transmit electric current to the human body. The corresponding indicator lamps (323) indicate operation of such devices. The heating curing plates (34) are connected to the power source by inserting to the heat curing plate connector (341) to generate heat for curing purposes. The electric therapeutic devices (33) and the heat curing plates (34) can be applied to the human body at the respective acupuncture points as indicated on the display (26) for therapy purposes.

3. The power supply (4) is composed of an AC to DC transformer (41) and a rechargeable battery or dry battery (42). The transformer (41) is to transform alternating current to direct current to provide a power source for the present invention via the power source socket (18). The rechargeable battery (42) is to provide a power source upon failure of city power or for operation at place without city power.

Figure 3:
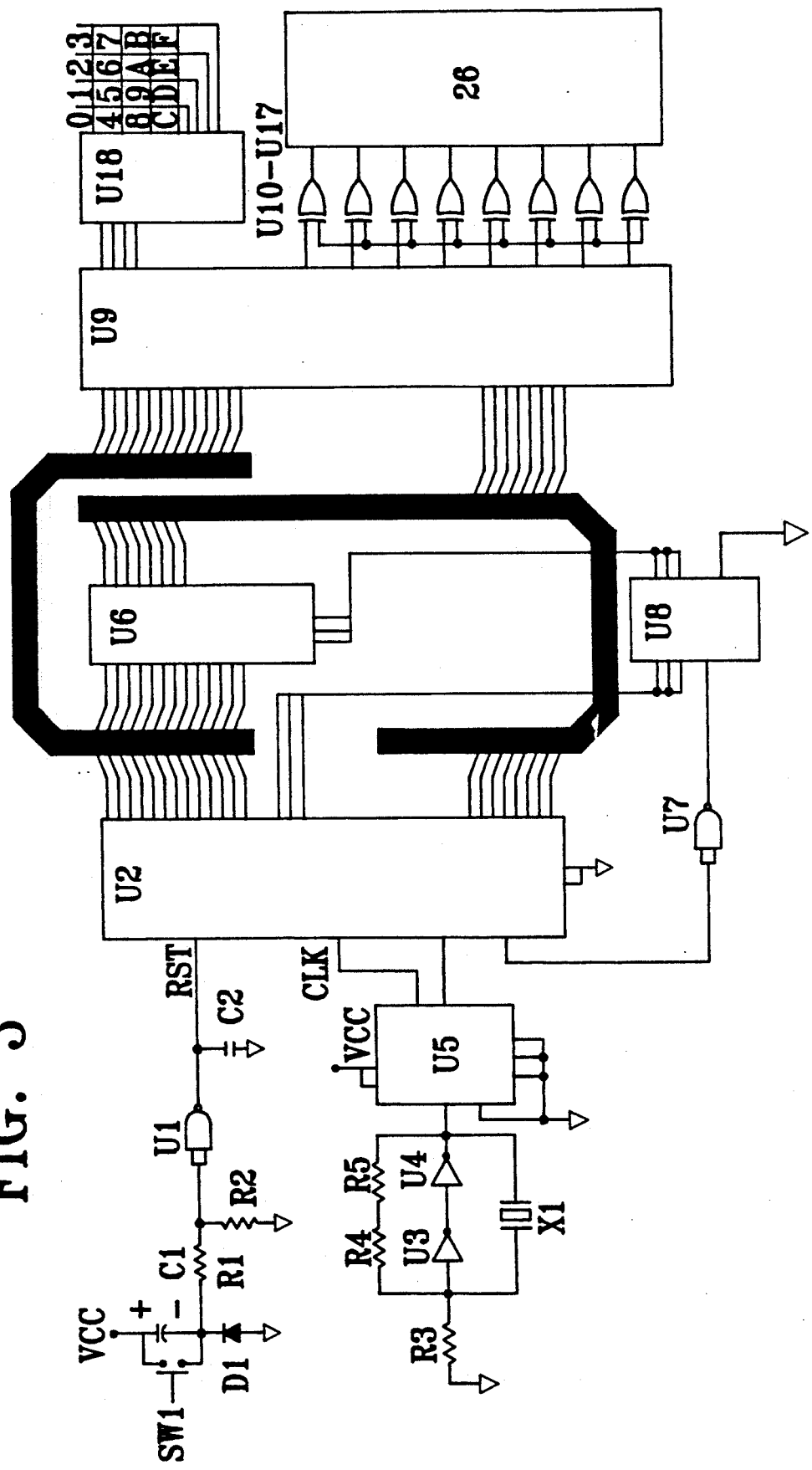
FIG. 3 is a circuit diagram of the acupuncture point display system for the acupuncture point display type electric stimulating therapeutic device according to the present invention.

Please refer to FIG. 3, a circuit diagram of the acupuncture point display system for the acupuncture point display type electric stimulating therapeutic device according to the present invention, the reset switch SW1 is designed to send a reset signal via two capacitors C1 and C2, a diode D1, two resistors R1 and R2, and a driver U1 to a single-chip microprocessor U2 which is serving as a control center of the present invention. The time sequence generator U5 and the corresponding oscillator X1, resistors R3, R4 and R5, and drivers U3 and U4 are to generate a sequence pulse to drive the microprocessor U2 for operation. Upon control by the microprocessor U2, a driver U7 and a buffer U8 retrieves the corresponding data from a memory U6, an electric programmable read only memory where data about acupuncture points are stored. In the diagram, U9 is a data input/output port, and U18 is a 16-bit coder for a keyboard.

Upon operation of the system, after a code is given to the encoder U18 via the keyboard, a binary input is sent to the input/output port U9 via the bus wire, converted to a parallel data, and then sent to the microprocessor U2 as well as the memory U6 so that the microprocessor U2 can, with a preset program, give a control signal via the driver U7 and the buffer U8 to the read only memory U6 for retrieval of data required. The data so retrieved is delivered via the input/output port U9, exclusive-OR gates U10–U17 and then displayed on the LCD display 26. A menu of disorder is first displayed, from which the code (A4) of the disorder or disease to be treated can be found. Then, by entering the code via the decoder U18, the input/output port U9, the memory U6 and the microprocessor U2, related data stored in the memory U6 is retrieved with the preset program, the data is sent via the input/output port U9, and the exclusive-OR gates U10–U17 to the display (26) for display. On the display 26, a description of the disorder, name and location of the related acupuncture points, and a figure showing positions of such acupuncture points are displayed. For example, when a code A4 is entered via the keyboard as shown in FIG. 1, the display (26) shows the following description (261):

Disorder: Shook
Code No.: A4
Name of Acupuncture Points: Neikuan, Tsusanli
Locations: Neikuan is located on outer side of each palm, 2 inches above the center of wrist joint. Tsusanli is located on outer side of tibia, 3 inches below the knee.

The figure (262) shows the locations of such acupuncture points on the human body. Hence, even if the operator is not familiar with the location of such acupuncture points, he can refer to the figure and apply the electric therapeutic devices (33) and heat curing plates (34) on such acupuncture points at the correct locations for therapy purposes.

As described above, the acupuncture point display type electric stimulating therapeutic device according to the present invention comprises a casing, an acupuncture point display system, an electric stimulating and heat generation system, and a power supply. The casing is divided into two parts: an upper casing and a lower casing. The upper casing has a hollow interior space, and has a recessed display, the lower casing has a number of control switches, adjusting knobs and connectors on the top surface, a power source socket on the right side, a box for holding electric therapeutic devices and heat curing plate in the bottom. The upper and lower casings are connected together by a connecting element and locked together in the form like a book by means of a tenon and a mortise. The acupuncture point display system is installed within the upper casing, the electric stimulating and heat generation system is located within the lower casing, and the power supply is to provide electric power to all the systems via the power source socket on the lower casing. By entering the code representing the disorder to be treated, a description of the disorder, names and locations of the acupuncture points and a figure showing the locations of such acupuncture points on human body are displayed as a reference for application of the electric therapeutic device and/or heat curing plate for therapy purpose.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. An acupuncture point display type electric stimulating therapeutic device comprising:

a casing, divided into an upper casing and a lower casing connected together by a connecting element and fixed together by means of a tenon and a mortise, in which the upper casing defines a hollow interior space with a recessed display and a tenon thereon; the lower casing has a hollow interior space, a power source switch, a reset switch, an input device, a plurality of voltage regulating knobs, frequency regulating knobs, indicator lamps, electric therapeutic device connectors and heat curing plate connectors, and a mortise adapted to be engaged by the tenon;

an acupuncture point display system comprising an input device, an input/output port, a microprocessor, a memory, a time sequence generator, and a display, in which the input device is located on a top surface of the lower casing, the display is located on a surface of the upper casing, and the input/output port, the microprocessor, the memory and the time sequence generator are located within the upper casing such that when a code representing a disorder to be treated is entered through the input device and the input/output port to the microprocessor and the memory, related data is retrieved from the memory with a preset program and then a description of the disorder, names and locations of the related acupuncture points, and a figure showing the positions of such acupuncture points on a human body are displayed on the display;

an electric stimulating and heat generation system comprising a low frequency generator, a plurality of regulators and electric therapeutic devices and heat curing plates, in which the low frequency generator and the regulators are located within the lower casing, the electric therapeutic devices and the heat curing plates are connected to their respective connectors on the lower casing, and the lower frequency generator generates a low frequency high voltage signal which is adjusted by the regulators to cause the electric therapeutic devices and heat curing plates to provide an electric stimulation and heating effect of appropriate strength; and a power supply to provide electric power to the aforesaid systems;

whereby the description of the disorder to be treated, names and locations of related acupuncture points, and the figure showing locations of such acupuncture points on the human body are displayed so that the electric therapeutic devices and heat curing plates can be applied to the human body at a correct position by referring to the figure after a code representing the disorder to be treated is entered via the input device.

2. An acupuncture point display type electric stimulating therapeutic device as claimed in claim 1 wherein the display comprises a LCD.

3. An acupuncture point display type electric stimulating therapeutic device as claimed in claim 1 wherein the input device comprises a keyboard.

4. An acupuncture point display type electric stimulating therapeutic device as claimed in claim 1 wherein the connecting element comprises two retaining rings and a bus wire for connection of the upper and lower casings and transmission of power and signals respectively.

5. An acupuncture point display type electric stimulating therapeutic device as claimed in claim 1 further comprising a plurality of sets of regulators, each set of regulators comprising a voltage regulating knob, a frequency regulating knob and an indicator lamp to adjust the voltage and frequency and to indicate operation of the electric stimulating therapeutic device respectively.

6. An acupuncture point display type electric stimulating therapeutic device as claimed in claim 1 further comprising a computer connection socket placed on a side of the upper casing to connect an external computer for display of locations of acupuncture points.

7. An acupuncture point display type electric stimulating therapeutic device as claimed in claim 1 further comprising a release button located on the lower casing so as to control engagement and disengagement between the tenon and the mortise.

8. An acupuncture point display type electric stimulating therapeutic device as claimed in claim 1 wherein the power supply comprises a dry battery to provide power to all systems in the device.

9. An acupuncture point display type electric stimulating therapeutic device as claimed in claim 1 wherein the lower casing further comprises a power source socket located on a side to connect to an AC to DC transformer for a built-in rechargeable battery to provide power to all systems in the device.

10. An acupuncture point display type electric stimulating therapeutic device as claimed in claim 1 wherein the lower casing further comprises a box located in a bottom portion to hold electric therapeutic devices and heat curing plates.

11. An acupuncture point display type electric stimulating therapeutic device as claimed in claim 1 wherein the electric therapeutic devices comprise stimulating electrodes and electric acupuncture needles for connection of the electric therapeutic device connectors located on the lower casing.

13. An acupuncture point display type electric stimulating therapeutic device as claimed in claim 1 wherein the display comprises a LED display.

13. An acupuncture point display type electric stimulating therapeutic device as claimed in claim 1 wherein the display comprises a graphic display.

14. An acupuncture point display type electric stimulating therapeutic device as claimed in claim 1 wherein the input device comprises a card reader.

* * * * *